US008651101B2

(12) United States Patent
Tanaka et al.

(10) Patent No.: US 8,651,101 B2
(45) Date of Patent: Feb. 18, 2014

(54) NEBULIZER KIT AND NEBULIZER

(75) Inventors: Shinya Tanaka, Mishima-gun (JP);
Susumu Kutsuhara, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/642,413

(22) PCT Filed: Mar. 1, 2011

(86) PCT No.: PCT/JP2011/054594
§ 371 (c)(1),
(2), (4) Date: Oct. 19, 2012

(87) PCT Pub. No.: WO2011/135914
PCT Pub. Date: Nov. 3, 2011

(65) Prior Publication Data
US 2013/0032143 A1  Feb. 7, 2013

(30) Foreign Application Priority Data

Apr. 28, 2010  (JP) ................................. 2010-103125

(51) Int. Cl.
*A61M 11/00*  (2006.01)
(52) U.S. Cl.
USPC ............ 128/200.21; 128/200.18; 128/203.12; 206/438
(58) Field of Classification Search
USPC ............ 128/200.12, 200.16, 200.17, 200.18, 128/200.21, 203.12, 203.15; 604/317; 220/603, 719, 731, 710.5; 206/438; 222/571; 239/343
See application file for complete search history.

(56) References Cited

U.S. PATENT DOCUMENTS

| 5,785,048 | A | * | 7/1998 | Koerner | ................... | 128/200.23 |
| 6,161,536 | A | * | 12/2000 | Redmon et al. | .......... | 128/200.14 |
| 7,581,718 | B1 | * | 9/2009 | Chang | ........................... | 261/78.2 |
| 8,286,629 | B2 | * | 10/2012 | Esaki et al. | .............. | 128/200.21 |
| 2005/0011514 | A1 | * | 1/2005 | Power et al. | ............. | 128/200.14 |
| 2008/0223361 | A1 | | 9/2008 | Nieuwstad | | |
| 2010/0147292 | A1 | * | 6/2010 | Hamaguchi et al. | ...... | 128/200.23 |

FOREIGN PATENT DOCUMENTS

| JP | 06-285168 A | 10/1994 |
| JP | 2003-190015 A | 7/2003 |
| JP | 2007-097830 A | 4/2007 |
| JP | 2009-219543 A | 10/2009 |
| WO | WO 2007040025 A1 * | 4/2007 |

OTHER PUBLICATIONS

Official Communication issued in International Patent Application No. PCT/JP2011/054594, mailed on Apr. 5, 2011.

* cited by examiner

*Primary Examiner* — Steven Douglas
(74) *Attorney, Agent, or Firm* — Keating & Bennett, LLP

(57) ABSTRACT

A nebulizer kit includes a case body, a flow channel formation member that covers an opening in an upper area of the case body, and a cylindrical aerosol discharge port that passes through a portion of the top surface of the flow channel formation member located toward the outer edge thereof. The case body and/or the flow channel formation member includes a rotation mechanism that, when the case body has overturned and the aerosol discharge port has become positioned on the lower side in the vertical direction of the top surface of the flow channel formation member, causes the case body to rotate in a circumferential direction to cause the aerosol discharge port to move away from a lower side in the vertical direction. Even if the nebulizer kit has overturned, a liquid within the nebulizer kit is prevented from spilling.

7 Claims, 6 Drawing Sheets

NEBULIZER KIT AND NEBULIZER

BACKGROUND OF THE INVENTION

1. Field of the Invention

The present invention relates to nebulizer kits and nebulizers.

2. Description of the Related Art

A nebulizer is a device for producing an aerosol by atomizing a liquid such as water, a saline solution, a drug solution for treating respiratory system conditions, or the like. A user takes the aerosol produced by the nebulizer into his/her body by sucking the aerosol through his/her mouth, nose, or the like. In recent years, attempts have been made to use such nebulizers to produce aerosols of vaccines for preventing measles and the like, which are then administered to users internally via the mouth and nose.

Typically, a nebulizer includes a main body apparatus having a compressor that produces compressed air, and a nebulizer kit that produces the aerosol by introducing the compressed air. JP H6-285168A or JP 2009-219543A are examples of background art documents disclosing such a nebulizer. The nebulizer kit is provided with a mouthpiece, a mask, or the like that serves as an inhalation assistance tool, donned by the user to suck the aerosol through his/her mouth, nose, or the like.

Before the nebulizer is used, the nebulizer kit is placed on a table or the like. A cover portion of the nebulizer kit is opened, and a liquid such as a drug solution is poured into the nebulizer kit. After this, but before a tube connected to the main body of the nebulizer is connected to the nebulizer kit, there are situations where the nebulizer kit is unintentionally overturned. There are also situations where the nebulizer kit is unintentionally overturned when inhalation is temporarily suspended and the nebulizer kit is set down. If the nebulizer kit is overturned, there are cases where the liquid held within the nebulizer kit is spilled. Because asthmatic drugs and the like are typically expensive, it is not desirable for such liquids to be spilled.

SUMMARY OF THE INVENTION

Preferred embodiments of the present invention provide a nebulizer kit and a nebulizer that prevent a liquid held within the nebulizer kit from being spilled even if the nebulizer kit is overturned.

A nebulizer kit according to a first preferred embodiment of the present invention includes a closed-ended, cylindrical case body including an opening in an upper end, within which an aerosol is produced; a cover-shaped flow channel formation member that is attached to the case body so as to cover the opening; and a cylindrical aerosol discharge port arranged to pass through a portion of the top surface of the flow channel formation member located toward the outer edge thereof.

The case body and/or the flow channel formation member is provided with a rotation mechanism that, when the case body has overturned on a predetermined placement surface and the aerosol discharge port has become positioned on the lower side in the vertical direction of the top surface of the flow channel formation member, causes the case body to rotate in a circumferential direction of the outer circumferential surface of the case body so that the position of the aerosol discharge port moves away from a lower side in the vertical direction.

A nebulizer kit according to a second preferred embodiment of the present invention is the nebulizer kit according to the aforementioned first preferred embodiment, where an extension member that extends outward in the diametric direction of the case body is provided in an outer surface of the case body and/or an outer surface of the flow channel formation member; a leading end of the extension member is positioned further outward in the diametric direction of the case body than a tangent defined on an outer circumferential surface of the case body in a location closest to the inner circumferential surface of the aerosol discharge port, when viewed from above; and the rotation mechanism includes the extension member.

A nebulizer kit according to a third preferred embodiment of the present invention is the nebulizer kit according to the aforementioned first preferred embodiment, wherein a weight portion is provided in the case body and/or the flow channel formation member; a straight line is defined by connecting an area of the outer circumferential surface of the case body that is closest to the inner circumferential surface of the aerosol discharge port and an area located directly opposite to the area in the outer circumferential surface of the case body, when viewed from above; the weight portion is disposed so that a center of gravity of the weight portion and the straight line do not overlap, when viewed from above; and the rotation mechanism is configured so as to include the weight portion.

A nebulizer kit according to a fourth preferred embodiment of the present invention is the nebulizer kit according to the aforementioned first preferred embodiment, wherein a grip that extends outward in the diametric direction of the case body is provided in an outer surface of the case body; the grip is disposed in a position that, when the flow channel formation member is attached to the case body, is shifted in the circumferential direction from the side on which the aerosol discharge port is provided, when viewed from above; and the rotation mechanism is configured so as to include the grip.

A nebulizer according to a preferred embodiment of the present invention includes a main body including a compressor that discharges compressed air; a compressed air tube portion through which the compressed air discharged by the compressor is led; and the nebulizer kit according to the aforementioned first preferred embodiment, to which one end of the compressed air tube portion is attached and that produces an aerosol.

According to the nebulizer and the nebulizer kit of various preferred embodiments of the present invention, it is possible to achieve a nebulizer kit and a nebulizer that prevent a liquid held within the nebulizer kit from spilling even if the nebulizer kit has overturned.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
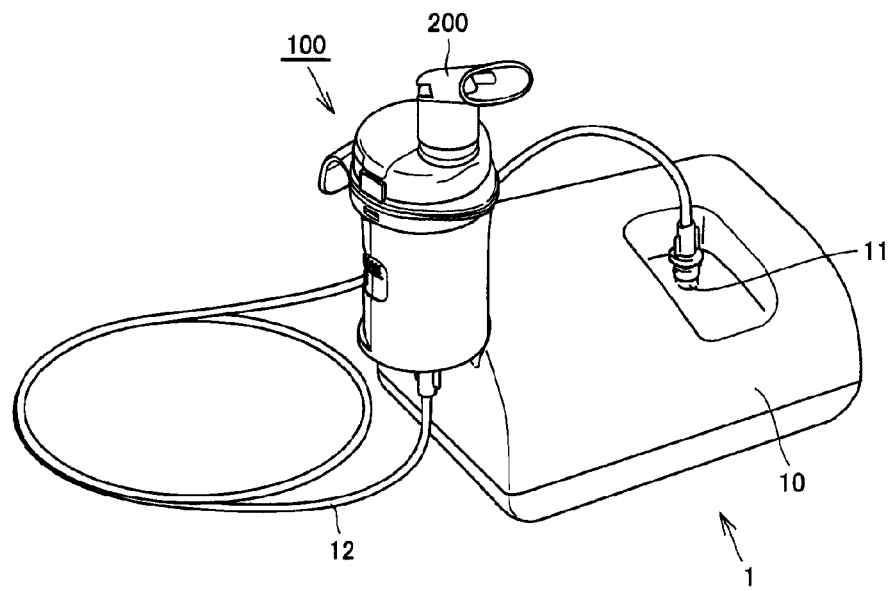
FIG. 1 is an overall perspective view illustrating the external configuration of a nebulizer according to a preferred embodiment of the present invention.

Hereinafter, a nebulizer kit and a nebulizer according to preferred embodiments of the present invention will be described in detail with reference to the drawings. When numbers, amounts, and so on are discussed below in the description of the preferred embodiments of the present invention, it should be noted that unless explicitly mentioned otherwise, the scope of the present invention is not necessarily limited to those numbers, amounts, and so on. In the drawings, identical reference numerals refer to identical or corresponding elements; there are also cases where redundant descriptions are omitted.

Hereinafter, a nebulizer 1 and a nebulizer kit 100 according to preferred embodiments will be described with reference to FIGS. 1 through 8. First, outlines of the configurations of the nebulizer 1 and the nebulizer kit 100 will be described with reference to FIGS. 1 through 5.

Figure 2:
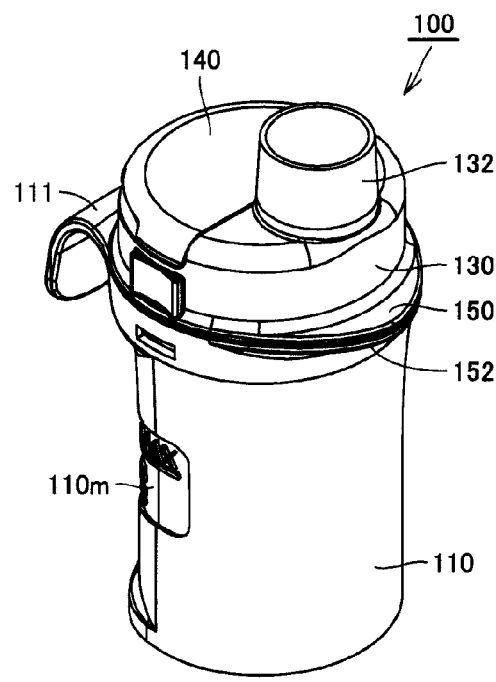
FIG. 2 is a first overall perspective view illustrating the external configuration of a nebulizer kit according to a preferred embodiment of the present invention.
Figure 3:
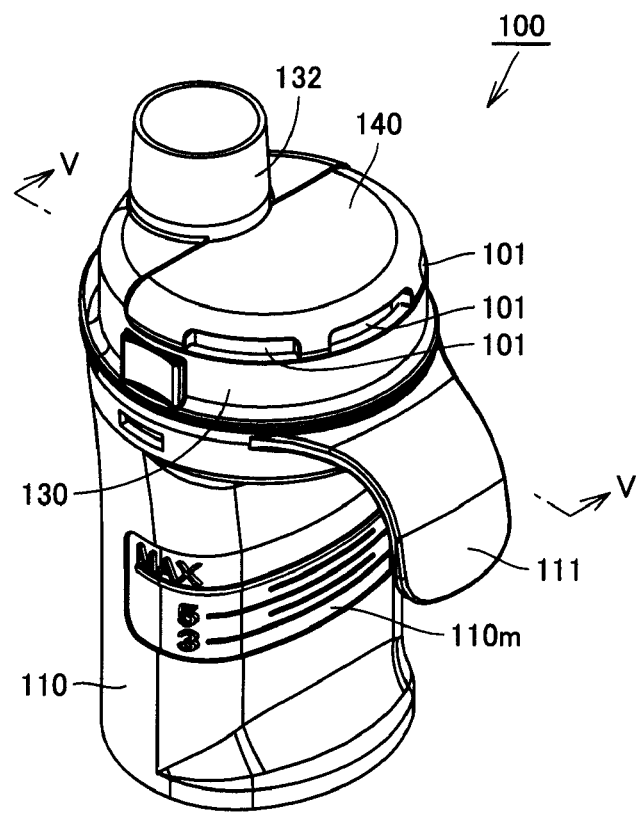
FIG. 3 is a second overall perspective view illustrating the external configuration of a nebulizer kit according to a preferred embodiment of the present invention.
Figure 4:
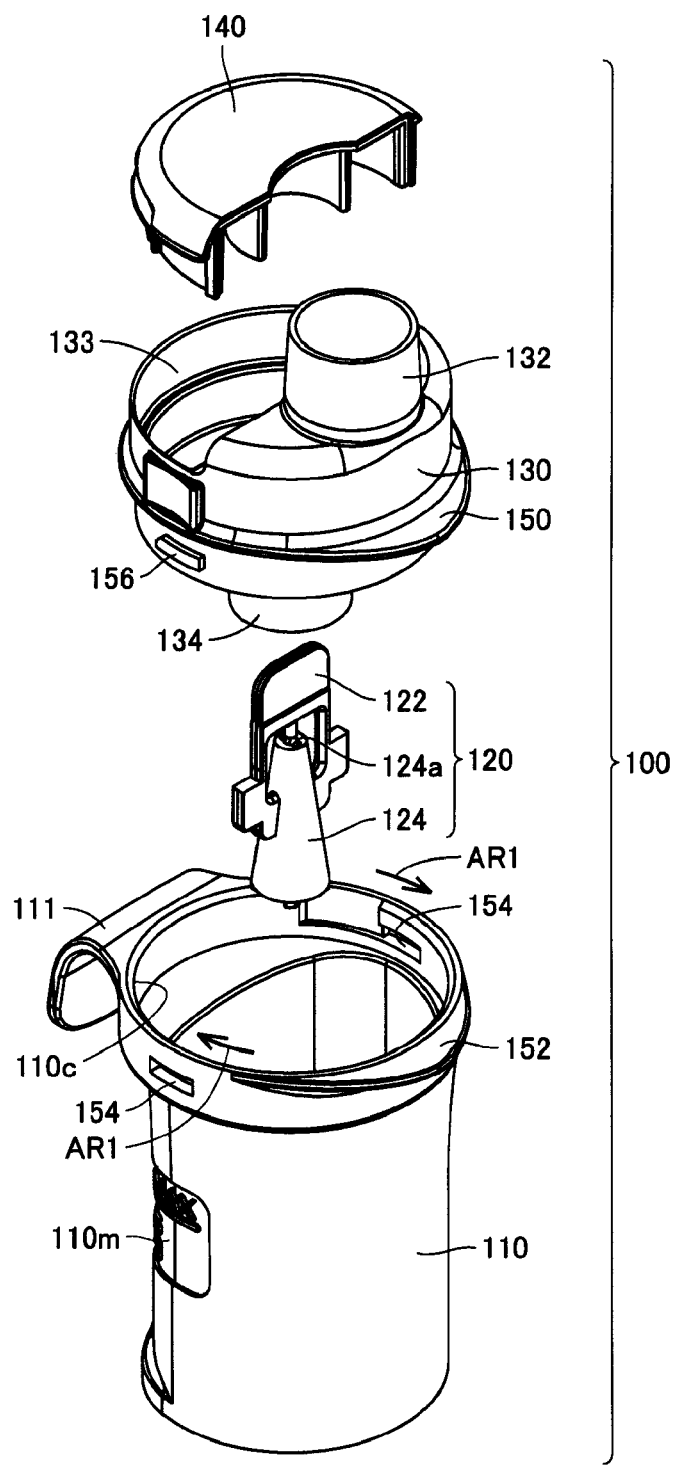
FIG. 4 is an exploded perspective view illustrating the nebulizer kit according to the preferred embodiment of the present invention.
Figure 5:
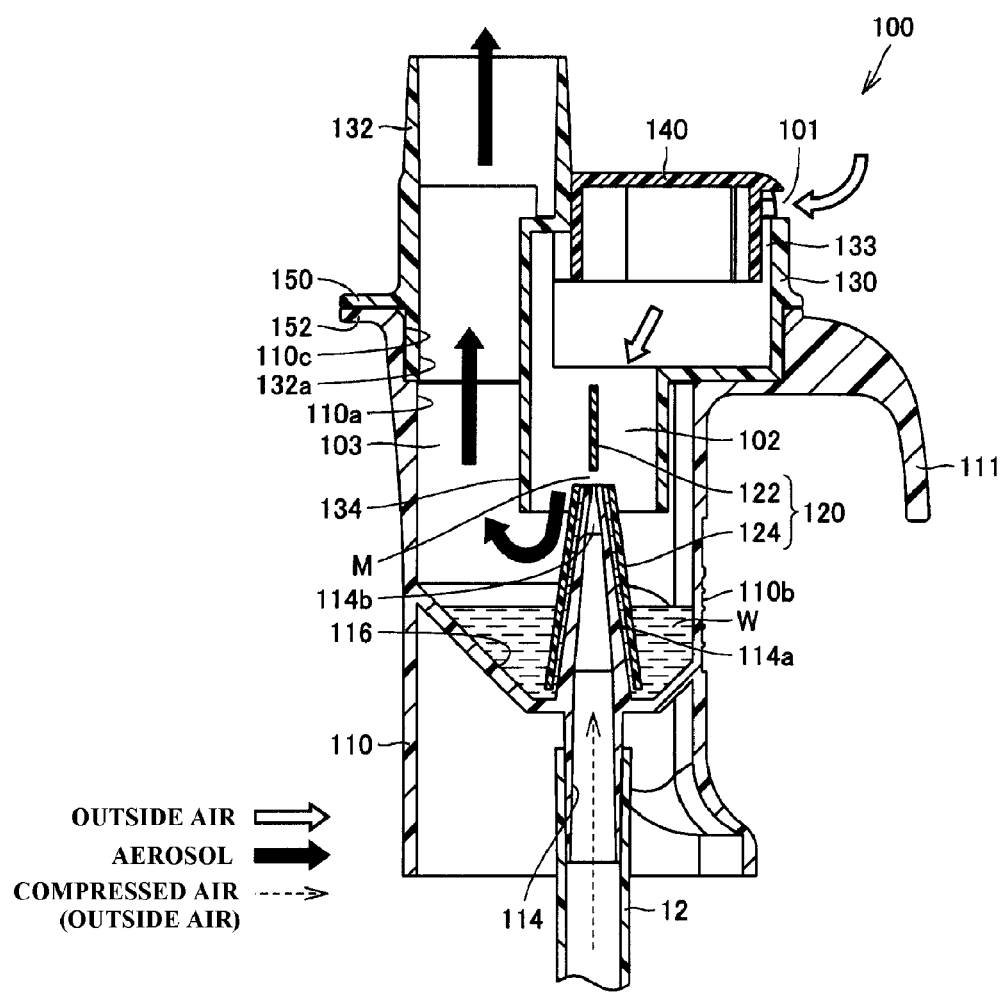
FIG. 5 is a vertical cross-sectional view taken along the V-V arrow in FIG. 3.

Note that FIG. 1 is an overall perspective view illustrating the external configuration of the nebulizer 1, FIGS. 2 and 3 are first and second overall perspective views illustrating the external configuration of the nebulizer kit 100, FIG. 4 is an exploded perspective view of the nebulizer kit 100, and FIG. 5 is a vertical cross-sectional view taken along the V-V arrow in FIG. 3.

As shown in FIG. 1, the nebulizer 1 preferably includes: a main body 10 that includes a compressor that emits compressed air, electrical components, and so on; a tube 12, serving as a flexible compressed air tube portion, whose one end is connected to a compressed air expulsion port 11 provided in the main body 10; the nebulizer kit 100, to which the other end of the tube 12 is connected; and a mouthpiece 200 that is connected to the nebulizer kit 100 and that serves as an inhalation assistance tool to assist a user to inhale from his or her mouth, nose, or the like. Various types of shapes are possible for the mouthpiece 200, such as a mask shape, for example.

As shown in FIGS. 2 through 5, the nebulizer kit 100 includes a case body 110, an atomizing area formation member 120 (see FIG. 4), a flow channel formation member 130, and a cap member 140. A cylindrical aerosol discharge port 132 is provided in the top surface of the flow channel formation member 130 so as to pass through a portion of the top surface of the flow channel formation member 130, and an inhalation assistance tool such as the mouthpiece 200 (see FIG. 1) is connected to this aerosol discharge port 132.

As shown in FIG. 3, a grip 111 is provided on the outer surface of the case body 110. The grip 111 extends outward from the stated outer surface in the diametric direction of the case body 110, and is configured so that the leading end side thereof curves downward.

When the flow channel formation member 130, mentioned later, is attached to the case body 110, the grip 111 is located on the side opposite to the side on which the aerosol discharge port 132 is provided, when viewed from above.

A scale 110*m* used to confirm the amount of a liquid such as a drug solution that is contained within the case body 110 is provided in the outer surface of the case body 110 below the grip 111. The scale 110*m* is provided on a wall surface of the case body 110 that faces outward so that the amount of liquid (that is, the content displayed by the scale 110*m*) can be easily seen from outside the case body 110. It is preferable to set the positional relationship between the grip 111 and the scale 110*m* so that the scale 110*m* is not visually obstructed by the grip 111. For example, it is preferable for the stated positional relationship to be set so that when the grip 111 is projected toward the side wall of the case body 110, the resulting projected image does not overlap with the scale 110*m* (see FIG. 5). Multiple pressure adjustment spaces 101 are provided between the cap member 140 and the flow channel formation member 130.

As shown in FIG. 4, the atomizing area formation member 120 includes: a conical liquid suction tube formation portion 124 that includes an opening portion 124*a* provided in the apex thereof; and a baffle 122 located immediately above the opening portion 124*a*.

The case body 110 includes an opening 110*c* at the upper end thereof, and is configured as a closed-ended cylinder. The atomizing area formation member 120 is contained and disposed within the case body 110. An engagement recess 154 is provided on the inner circumferential surface of the case body 110 toward the opening 110*c*, so as to extend along the circumferential direction.

The flow channel formation member 130 is configured so as to have a cover-like shape, and a protrusion 156 is provided in the outer circumferential surface at the lower end thereof, so as to extend along the circumferential direction. The flow channel formation member 130 is fitted into the upper area of the case body 110 so as to cover the opening 110*c* in the upper end of the case body 110.

The protrusion 156 and the engagement recess 154 are engaged with each other by rotating the flow channel formation member 130 in the direction of an arrow AR1 while the flow channel formation member 130 is fitted into the case body 110. The flow channel formation member 130 is attached to the upper area of the case body 110 through this engagement. The cap member 140 is then attached to the flow channel formation member 130 so as to cover an opening portion 133 provided in the top surface of the flow channel formation member 130.

As shown in FIG. 5, the aerosol discharge port 132 is provided in a location of the top surface of the flow channel formation member 130 that is offset toward the outer periphery (to the left, in the drawings). The direction in which the aerosol discharge port 132 extends (the vertical direction in the drawings) and the direction in which the flow channel formation member 130 extends (the vertical direction in the drawings) are in a positional relationship that is approximately parallel.

Because the flow channel formation member 130 and the aerosol discharge port 132 are in a positional relationship in which the directions in which those elements extend are approximately parallel, those elements can be produced by pulling a metal mold in a single direction (the vertical direction in the drawings), which increases the manufacturing efficiency.

For example, in the nebulizer kit disclosed in JP H6-285168A, an aerosol discharge port is protrudes from a side surface of a case body, and thus the directions in which the stated elements extend intersect with each other. It is necessary to produce the nebulizer kit disclosed in JP H6-285168A by pulling metal molds in two directions, and thus, the manufacturing efficiency is poor.

Returning once again to FIG. 5, when the flow channel formation member 130 is attached to the case body 110, a portion 132a of the inner circumferential surface of the aerosol discharge port 132 inscribes a portion 110a of the inner circumferential surface of the case body 110 when viewed from above. The area inscribed by the portions 110a and 132a when viewed from above defines an approximate straight line that is continuous when viewed as a cross-section, and extends toward a side in which a reservoir portion 116, mentioned later, is provided.

A plate-shaped member is provided on neither the inner circumferential surface of the aerosol discharge port 132 nor the inner circumferential surface of the case body 110 in an area extending in an approximately straight line toward the side in which the reservoir portion 116 is provided, the approximately straight line being formed by continuations of the parts 110a and 132a. The aerosol discharge port 132 has an aerosol transport channel 103 (details will be given later) that secures a sufficient flow channel area, and thus has a favorable aerosol discharge efficiency.

In, for example, the nebulizer kit disclosed in JP 2009-219543A, a plate-shaped member that protrudes toward the inside of the aerosol discharge port 132 is provided (see FIG. 3 of JP 2009-219543A). This plate-shaped member protrudes above the inner circumferential surface of the aerosol discharge port. Providing this plate-shaped member in the inner circumferential surface of the aerosol discharge port reduces the flow channel area that serves as the aerosol transport channel. The nebulizer kit in JP 2009-219543A has a poor aerosol discharge efficiency.

The case body 110, the atomizing area formation member 120, the flow channel formation member 130, the cap member 140, and the tube 12 can be separated from each other and reassembled, and the configuration is therefore such that the nebulizer 1 can be washed and sterilized with ease after use. Furthermore, the inhalation assistance tool, such as the mouthpiece 200, preferably is a disposable type, and is discarded after use for sanitary reasons.

As shown in FIG. 5, an outside air introduction tube 134 that connects to an opening portion of the aerosol discharge port 132 is provided in the base surface of the flow channel formation member 130. A compressed air introduction tube 114 that introduces compressed air discharged from a compressor through the compressed air expulsion port 11 (see FIG. 1) and the tube 12 into the interior of the case body 110 is provided in the base surface of the case body 110 so as to extend in the vertical direction.

The tube 12 is attached to the lower leading end area of the compressed air introduction tube 114. Meanwhile, an upper leading end area 114a of the compressed air introduction tube 114 preferably has a shape that tapers toward a leading end opening 114b.

The reservoir portion 116 is provided in the periphery of the area of the case body 110 where the compressed air introduction tube 114 is formed. The reservoir portion 116 temporarily holds a liquid W such as water, a saline solution, a drug solution for treating respiratory system conditions or the like, a vaccine, or the like.

The liquid suction tube formation portion 124 of the atomizing area formation member 120 is mounted so as to cover the upper leading end area 114a of the compressed air introduction tube 114; the leading end opening 114b of the compressed air introduction tube 114 is exposed from the opening portion 124a of the liquid suction tube formation portion 124, and opposes the baffle 122 in the atomizing area formation member 120.

Next, the production and discharge of aerosol will be described with reference to FIG. 5. Note that in FIG. 5, the broken line arrow indicates the flow of compressed air (outside air) discharged from the main body 10 (see FIG. 1) of the nebulizer 1, the white arrow indicates the flow of outside air introduced from the pressure adjustment spaces 101, and the black arrow indicates the discharge flow of the aerosol.

A liquid suction tube is configured by the gap between the liquid suction tube formation portion 124 and the upper leading end area 114a of the compressed air introduction tube 114, and the liquid W held in the reservoir portion 116 reaches the vicinity of an atomizing area M, which will be mentioned later, under the effect of a negative pressure caused by the blowing of the compressed air, which will also be mentioned later.

The atomizing area M is located between the upper leading end area 114a of the compressed air introduction tube 114 and the baffle 122. At the atomizing area M, compressed air introduced into the compressed air introduction tube 114 by the main body 10 of the nebulizer 1 is blown from the upper leading end area 114a of the compressed air introduction tube 114 toward the baffle 122. At this time, the liquid W sucked upward to the vicinity of the atomizing area M due to the effects of negative pressure produced at the atomizing area M is blown upward toward the atomizing area M due to the stated effects of the negative pressure and is blown toward the baffle 122 along with the compressed air.

Due to these effects, the liquid W turns into fine liquid droplets upon colliding with the baffle 122, becoming mist particles as a result; these mist particles are added to the outside air introduced into the case body 110 (this includes outside air introduced by the main body 10 of the nebulizer 1 as mentioned above, as well as outside air introduced from the pressure adjustment spaces 101 (mentioned later) based on suction actions performed by a user), thus producing an aerosol within the case body 110.

The flow channel formation member 130 and the cap member 140 are positioned and disposed above the atomizing area formation member 120. The inner space of the case body 110 is partitioned and a flow channel through which air flows is defined by the flow channel formation member 130. In addition, the cap member 140 is fitted into the opening portion 133 provided in the top surface of the flow channel formation member 130, and the pressure adjustment spaces 101, which allow the space within the nebulizer kit to communicate with the exterior, are defined by the gap between the flow channel formation member 130 and the cap member 140.

To be more specific, the space within the case body 110 is partitioned into a central space and a peripheral edge space by the outside air introduction tube 134 provided in the lower area of the flow channel formation member 130; an outside air introduction channel 102 is defined by the inner side of the outside air introduction tube 134, whereas the aerosol transport channel 103 is defined by a region enclosed by the outer side of the outside air introduction tube 134 and the case body 110.

The outside air introduction channel 102 is a flow channel that leads outside air that has flown in from the pressure adjustment spaces 101 to the atomizing area M, whereas the aerosol transport channel 103 is a flow channel that leads the aerosol produced at the atomizing area M to the aerosol discharge port 132. Note that as mentioned above, a plate-shaped member is provided in neither the inner circumferential surface of the aerosol discharge port 132 nor the inner circumferential surface of the case body 110 along the aerosol transport channel 103.

Meanwhile, the case body 110 according to the present preferred embodiment includes a wall surface 110b on the side of the case body 110, which encloses the outside air introduction tube 134, that is opposite to the side on which the aerosol discharge port 132 is provided, when viewed from the atomizing area M.

The wall surface of the case body 110 on the side on which the aerosol discharge port 132 is provided when viewed from the atomizing area M preferably has an approximately semicircular shape, and a straight line portion (a planar surface when viewed three-dimensionally) is provided in the wall surface of the case body 110 on the opposite side as the side in which the aerosol discharge port 132 is provided, when viewed from the atomizing area M.

By providing the wall surface 110b having the straight line portion in the case body 110, the wall surface 110b serves as a barrier, making it possible to actively change the flow of the aerosol from flowing from the outside air introduction channel 102 in a direction moving away from the aerosol discharge port 132 to a direction moving toward the aerosol discharge port 132.

Meanwhile, the area (volume) of the opening located toward the side of the aerosol discharge port 132 when viewed from the atomizing area M is greater than the area (volume) of the opening located on the opposite side as the aerosol discharge port 132 when viewed from the atomizing area M. As a result, the discharge resistance of the aerosol is lower toward the aerosol discharge port 132 and greater on the opposite side as the aerosol discharge port 132. Accordingly, the aerosol is discharged more toward the aerosol discharge port 132.

Next, an extension member 152 and an extension member 150 will be described in that order with reference to FIGS. 4 and 5. The extension member 152 is provided on the outer surface of the upper end side of the case body 110. The extension member 152 according to the present preferred embodiment extends, in a flat plate shape, outward from the case body 110 in the diametric direction thereof. The extension member 152 may be formed integrally with the case body 110, or may be formed as a separate entity from the case body 110 and attached thereto later.

The leading end side of the extension member 152 configures a semicircular arc shape when viewed from above. Both ends of the extension member 152 are configured so as to extend along tangential directions (see tangents LN1 and LN2 in FIG. 7) at the areas corresponding to those both ends on the outer circumferential surface of the case body 110.

When the flow channel formation member 130 is attached to the case body 110, the extension member 152 is located on the side on which the aerosol discharge port 132 is provided, when viewed from above.

The extension member 150 is provided on the outer surface of the lower end side of the flow channel formation member 130. The extension member 150 according to the present preferred embodiment extends, in a flat plate shape, outward from the case body 110 in the diametric direction thereof. The extension member 150 may be formed integrally with the flow channel formation member 130, or may be formed as a separate entity from the flow channel formation member 130 and attached thereto later.

The leading end side of the extension member 150 configures a semicircular arc shape when viewed from above. Both ends of the extension member 150 are configured so as to extend along tangential directions (see the tangents LN1 and LN2 in FIG. 7) at the areas corresponding to those both ends on the outer circumferential surface of the flow channel formation member 130.

When the flow channel formation member 130 is attached to the case body 110, the extension member 150 is located on the side on which the aerosol discharge port 132 is provided, when viewed from above.

The extension member 150 and the extension member 152 according to the present preferred embodiment preferably have approximately the same shape, and, when viewed from above, overlap with each other when the flow channel formation member 130 is attached to the case body 110.

As mentioned above, the flow channel formation member 130 is rotated in the direction of the arrow AR1 (see FIG. 4) in a state in which the flow channel formation member 130 is fitted into the case body 110. The configuration is such that when the engagement recess 154 (see FIG. 4) and the protrusion 156 (see FIG. 4) are engaged, the extension member 150 and the extension member 152 overlap with each other, which provides the user with a visual sense of relief. In addition, by confirming that the extension member 150 and the extension member 152 are overlapping with each other as a result of the rotation, the user can easily fit the flow channel formation member 130 into the case body 110 after positioning those elements relative to each other.

In addition, the extension members 150 and 152 extend outward from the case body 110 in the diametric direction thereof. The user can hook his/her finger onto the extension members 150 and 152. Accordingly, using the extension members 150 and 152, the user can easily rotate the flow channel formation member 130 relative to the case body 110 in the direction of the arrow AR1 (see FIG. 4).

Figure 6:
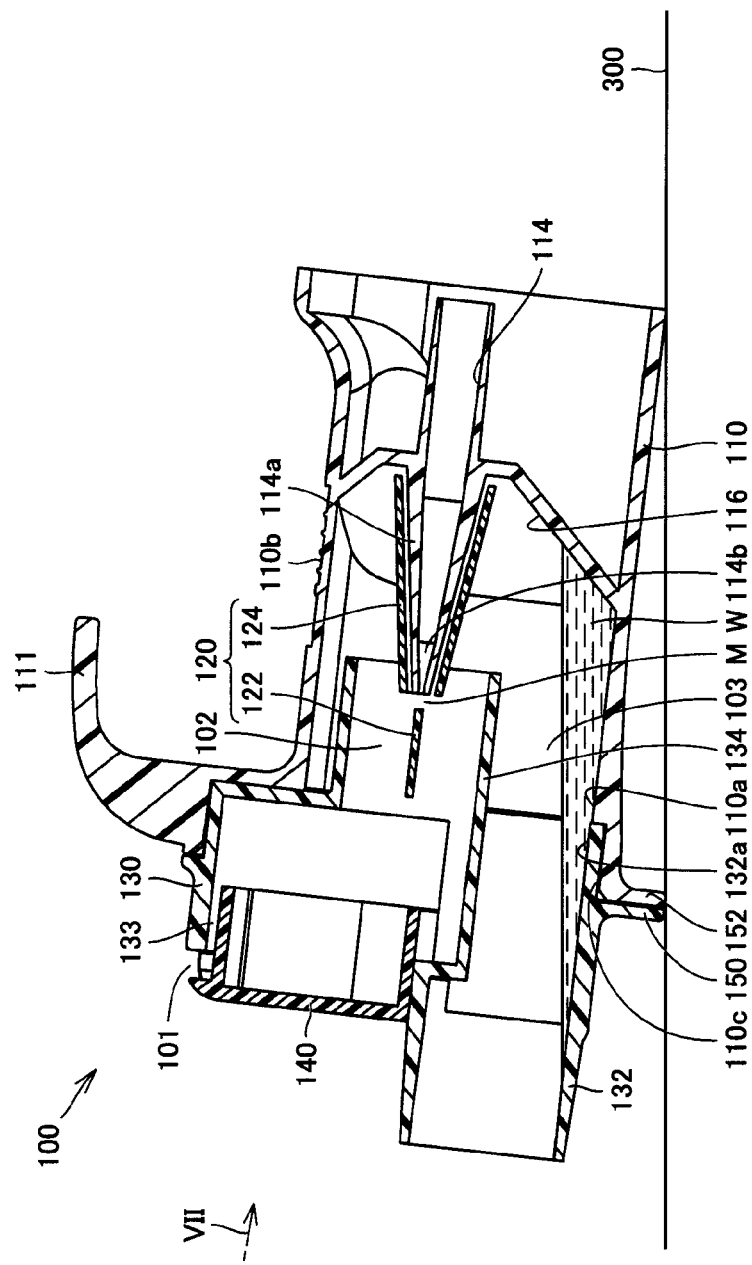
FIG. 6 is a cross-sectional view illustrating the nebulizer kit in an overturned state according to a preferred embodiment of the present invention.
Figure 7:
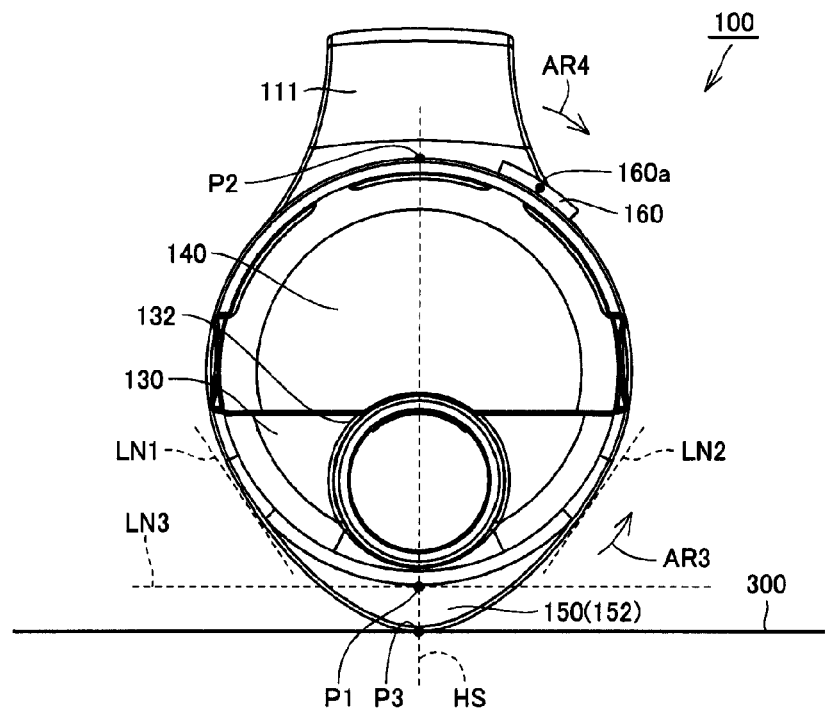
FIG. 7 is a plan view illustrating a nebulizer kit according to a preferred embodiment of the present invention from the direction of the VII arrow shown in FIG. 6, and illustrating a nebulizer kit according to another aspect of a preferred embodiment of the present invention.
Figure 8:
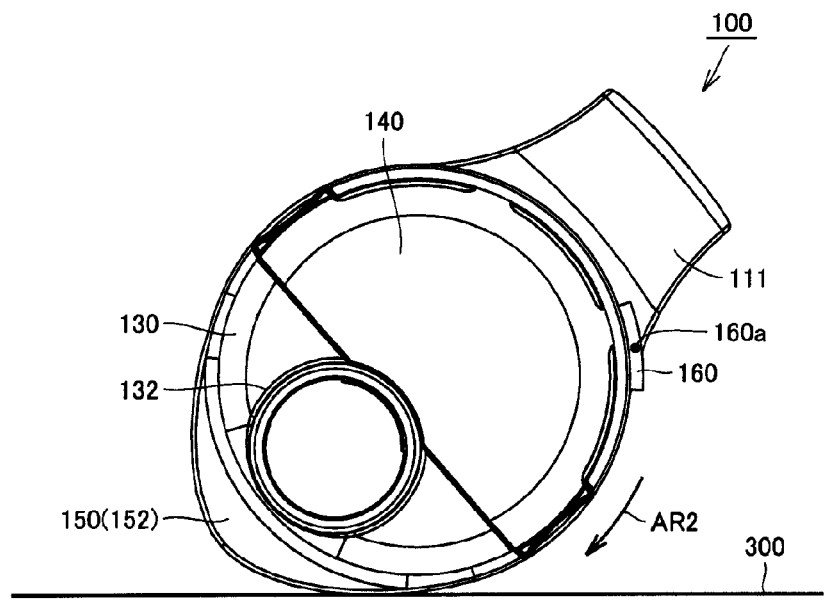
FIG. 8 is a plan view illustrating the nebulizer kit according to a preferred embodiment of the present invention rotating in the circumferential direction of an outer circumferential surface of a case body.

Next, operations when the nebulizer kit 100 is overturned will be described with reference to FIGS. 6 through 8. FIG. 6 is a cross-sectional view illustrating a state in which the nebulizer kit 100 that has been placed on a placement surface 300 such as a table has been overturned onto the side in which the aerosol discharge port 132 is provided when viewed from above. FIG. 7 is a plan view illustrating the nebulizer kit 100 in FIG. 6 from the direction of an arrow VII. FIG. 8 is a plan view illustrating the nebulizer kit 100 rotating in the circumferential direction of the outer circumferential surface of the case body 110.

As shown in FIGS. 6 and 7, when the nebulizer kit 100 is overturned onto the side in which, when viewed from above, the aerosol discharge port 132 is provided, the liquid W held in the reservoir portion 116 can easily spill from the aerosol discharge port 132.

In this state, the case body 110 is tilted greatly from the vertical direction (that is, the direction perpendicular or substantially perpendicular to the placement surface 300), and the upper end of the aerosol discharge port 132 is positioned below the upper surface of the flow channel formation member 130 in the vertical direction (on the lower side in FIG. 7).

The nebulizer kit 100 according to the present preferred embodiment includes the extension member 152 and the extension member 150 as a rotation mechanism. When the nebulizer kit 100 is overturned as described above, the vicinity of the leading ends of the extension member 150 and the extension member 152 (that is, the area P3 in FIG. 7) makes contact with the placement surface 300.

If, for example, the nebulizer kit 100 stops in this state (without rotating in the circumferential direction), the liquid W will spill from the aerosol discharge port 132, depending on the amount of the liquid W. However, the extension members 150 and 152 according to the present preferred embodiment serve as a rotation mechanism and cause the case body 110 to rotate in the circumferential direction.

This will be described in detail with reference to FIG. 8. As described above, the leading end sides of the extension members 150 and 152 according to the present preferred embodiment configure a semicircular arc shape when viewed from above. Furthermore, as described above, both ends of the extension members 152 and 150 are configured so as to extend along tangential directions (tangents LN1 and LN2) at the areas corresponding to those both ends on the outer circumferential surface of the case body 110.

By configuring the extension members 150 and 152 as described above, a propulsive force that actively causes the case body 110 to rotate in the circumferential direction (without stopping the case body 110) acts on the overturned case body 110. Due to this propulsive force, the nebulizer kit 100 (case body 110) rotates smoothly and quickly in the direction of the arrow AR2 (the circumferential direction) while the peripheral edges of the extension members 150 and 152 make contact with the placement surface 300, and thus the position of the aerosol discharge port 132 moves away from the lower side of the top surface of the flow channel formation member 130 in the vertical direction.

When the position of the aerosol discharge port 132 moves away from the lower side of the top surface of the flow channel formation member 130 in the vertical direction, the position of the opening portion in the leading end of the aerosol discharge port 132 rises, and the liquid W held within the nebulizer kit 100 moves away from the position of the opening portion in the leading end of the aerosol discharge port 132. As a result, the liquid W is prevented from spilling from the opening portion in the leading end of the aerosol discharge port 132.

By providing the grip 111 in the outside surface of the case body 110, the grip 111 not only improves the convenience for the user when using the nebulizer 1, but can also function as a stopper during the stated rotation of the nebulizer kit 100. The grip 111 makes contact with the placement surface 300 when the overturned nebulizer kit 100 rotates (for example, approximately 180° in the circumferential direction). Due to this contact, the grip 111 prevents the nebulizer kit 100 from rotating further in the circumferential direction.

As described above, it is preferable for the grip 111 to be positioned on the opposite side as the side on which the aerosol discharge port 132 is provided, when viewed from above. The grip 111 can function as a stopper even when provided in another location, such as a location that is shifted in the circumferential direction from the side on which the aerosol discharge port 132 is provided, when viewed from above. From the standpoint of preventing the liquid W held within the nebulizer kit 100 from spilling, the grip 111 may be provided in a location that is close to the aerosol discharge port 132, when viewed from above. In order for the grip 111 to most effectively achieve both the original function of a grip and a function of preventing the liquid W from spilling, it is preferable for the grip 111 to be provided in a location that is the furthest away from the aerosol discharge port 132, when viewed from above. In the case where the nebulizer kit 100 includes the grip 111, the rotation mechanism is configured so as to include the extension members 150 and 152 and the grip 111.

As shown in FIGS. 7 and 8, the nebulizer kit 100 may include a weight portion 160. Note that the weight portion 160 is not shown in FIGS. 1 through 6. In this case, the weight portion 160 may be provided on one of the case body 110 and the flow channel formation member 130, or may be provided on both.

The weight portion 160 according to the present preferred embodiment is configured as a flat plate-shaped member that extends in the vertical direction in FIG. 7, and is attached to the outer circumferential surface of the case body 110. The location of a center of gravity 160*a* of the weight portion 160 is shifted in the circumferential direction (the direction of the arrow AR3 in FIG. 7) relative to an area P1 (details will be given later) located on the side where the aerosol discharge port 132 is provided, when viewed from above. Furthermore, the location of the center of gravity 160*a* of the weight portion 160 is shifted in the circumferential direction (the direction of the arrow AR4 in FIG. 7) relative to an area P2 that is directly opposed to the side on which the aerosol discharge port 132 is provided, when viewed from above (to rephrase, is located directly opposite to the area P1).

By configuring the weight portion 160 as described above, a propulsive force that actively causes the case body 110 to rotate in the circumferential direction acts on the overturned case body 110. The nebulizer kit 100 (case body 110) rotates smoothly and quickly in the direction of the arrow AR2 (see FIG. 8) while the peripheral edges of the extension members 150 and 152 make contact with the placement surface 300, and thus the position of the aerosol discharge port 132 moves away from the lower side of the top surface of the flow channel formation member 130 in the vertical direction.

When the position of the aerosol discharge port 132 moves away from the lower side of the top surface of the flow channel formation member 130 in the vertical direction, the position of the opening portion in the leading end of the aerosol discharge port 132 rises, and the liquid W held within the nebulizer kit 100 moves away from the position of the opening portion in the leading end of the aerosol discharge port 132. As a result, the liquid W is prevented from spilling from the opening portion in the leading end of the aerosol discharge port 132.

The weight portion 160 may, from the standpoint of producing the stated propulsive force, be provided in a different position than the aforementioned position. The weight portion 160 may, for example, be provided on the inner circumferential surface of the case body 110, on the inner circumferential surface of the flow channel formation member 130, or on the outer circumferential surface of the flow channel formation member 130, or may be provided in a plurality of these locations.

The weight portion 160 may be provided on the base surface of the case body 110. The weight portion 160 may be provided on the top surface of the flow channel formation member 130, or may be attached to the grip 111. The weight portion 160 may, through insert molding or the like, be embedded within a member that configures the case body 110, the flow channel formation member 130, the grip 111, or the like.

The location of the weight portion 160 is not limited to the aforementioned location, and the weight portion 160 may further be provided in another location. When viewed from above, a straight line HS (or a plane, when viewed three-dimensionally) is defined by connecting the area P1 on the outer circumferential surface of the case body 110 that is closest to the inner circumferential surface of the aerosol discharge port 132 with the area P2 that is located directly opposite to the area P1 on the outer circumferential surface of the case body 110. The weight portion 160 may, when viewed from above, be disposed so that the center of gravity 160*a* of the weight portion 160 and the stated straight line HS do not overlap (that is, so that the position of the center of gravity 160*a* of the weight portion 160 does not fall on the stated straight line HS).

By disposing the weight portion 160 so that the position of the center of gravity 160a is as described above, a propulsive force that actively causes the case body 110 to rotate in the circumferential direction acts on the overturned case body 110. In the case where the nebulizer kit 100 includes the weight portion 160, the rotation mechanism is configured so as to include the weight portion 160.

The nebulizer kit 100 may include all of the extension member 150, the extension member 152, and the weight portion 160, or may include at least only one of these elements. To rephrase, the nebulizer kit 100 may be configured so that the rotation mechanism does not include the extension members 150 and 152, and instead includes only the weight portion 160. The rotation mechanism may be configured including only the extension member 150, may be configured including only the extension member 152, or may be configured including only the weight portion 160. The rotation mechanism may be configured so as to include the grip 111, along with one or more of the extension member 150, the extension member 152, and the weight portion 160. Furthermore, the rotation mechanism may be configured including only the grip 111. In the case where the rotation mechanism is configured including only the grip 111, it is preferable, for example, for the location of the center of gravity of the grip 111 to be disposed so that a propulsive force that actively causes the case body 110 to rotate in the circumferential direction acts upon the case body 110, in the same manner as the aforementioned center of gravity 160a of the weight portion 160. Note that the nebulizer kit 100 need not include the grip 111.

As shown in FIGS. 5 and 6, according to the nebulizer 1 and the nebulizer kit 100, the rotation mechanism causes the nebulizer kit 100 (the case body 110) to rotate in the circumferential direction, even if the nebulizer kit 100 has overturned. As a result, the liquid W held within the nebulizer kit 100 is prevented from spilling.

According to the nebulizer 1 and the nebulizer kit 100, a plate-shaped member is provided in neither the inner circumferential surface of the aerosol discharge port 132 nor the inner circumferential surface of the case body 110 along the aerosol transport channel 103. Compared to, for example, the nebulizer kit disclosed in JP 2009-219543A (FIG. 3), the aerosol discharge port 132 secures a sufficient flow channel area for the aerosol transport channel 103, and thus the aerosol discharge efficiency is favorable.

According to the nebulizer 1 and the nebulizer kit 100, by providing the wall surface 110b having the straight line portion in the case body 110, the wall surface 110b serves as a barrier, making it possible to actively change the flow of the aerosol from flowing from the outside air introduction channel 102 in a direction moving away from the aerosol discharge port 132 to a direction moving toward the aerosol discharge port 132. The aerosol is discharged more toward the aerosol discharge port 132.

As shown in FIGS. 4 and 5, the leading end side of the extension members 150 and 152 in the aforementioned preferred embodiment preferably configures a semicircular arc shape when viewed from above. The extension members 150 and 152 preferably may be configured as triangular plate-shaped members having their apexes in the leading end side that extends, when viewed from above. The extension members 150 and 152 may also preferably be configured as triangular plate-shaped members having rounded apexes in the leading end that extends, when viewed from above.

The extension members 150 and 152 are not limited to plate-shaped members, and may be configured so as to extend in a rod shape outward in the diametric direction, or may be configured so as to protrude in a dome shape outward in the diametric direction. The extension members 150 and 152 may be configured so as to be horizontally symmetrical when viewed from above, or may be configured so as to be horizontally asymmetrical when viewed from above.

When the flow channel formation member 130 is attached to the case body 110, the extension members 150 and 152 according to the aforementioned preferred embodiment are located on the side on which the aerosol discharge port 132 is provided, when viewed from above.

As shown in FIG. 7 and described above, the area P1 on the outer circumferential surface of the case body 110 that is closest to the inner circumferential surface of the aerosol discharge port 132 is defined on the outer circumferential surface of the case body 110, when viewed from above. A tangent LN3 (a plane, when viewed three-dimensionally) is defined on the outer circumferential edge of the case body 110 at this area P1. In addition, the area P3 is defined at the leading end where the extension members 150 and 152 extend (the bottom in the drawings).

From the standpoint of preventing the liquid W held within the nebulizer kit 100 from spilling when the nebulizer kit 100 has overturned, it is preferable for the stated area P3 to be located further outward in the diametric direction of the case body 110 (the lower side, in FIG. 7) than the stated tangent LN3.

From the standpoint of further preventing the nebulizer kit 100 from stopping (that is, not rotating in the circumferential direction) when the nebulizer kit 100 has overturned, it is preferable for the stated area P3 to be located further outward in the diametric direction of the case body 110 (the lower side, in FIG. 7) than the stated tangent LN3, and for the stated area P3 to preferably have a semicircular arc shape or a parabolic shape when viewed from above.

As shown in FIG. 4, the extension member 152 according to the aforementioned preferred embodiment is preferably provided toward the upper end (the vertical direction, in the drawings) of the outer surface of the case body 110. The extension member 152 may be provided toward the center of the outer surface of the case body 110, or may be provided toward the lower end of the outer surface of the case body 110. The extension member 150 according to the aforementioned preferred embodiment is preferably provided toward the lower end (the vertical direction, in the drawings) of the outer surface of the flow channel formation member 130. The extension member 150 may be provided toward the center of the outer surface of the flow channel formation member 130, or may be provided toward the upper end of the outer surface of the flow channel formation member 130.

It is preferable for the design to be such that the extension members 150 and 152 or the weight portion 160 serving as the rotation mechanism can actively cause the overturned case body 110 to rotate in the circumferential direction, based on the shape of those elements and the location in which those elements are provided.

The foregoing has described exemplary preferred embodiments of the present invention, but it should be noted that the preferred embodiments disclosed above are to be understood as being in all ways exemplary and in no way limiting. The scope of the present invention is defined by the scope of the appended claims, and all changes that fall within the same essential spirit as the scope of the claims are intended to be included therein as well.

Further, while preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A nebulizer kit comprising:
a closed-ended, cylindrical case body that has an opening in an upper end, within which an aerosol is produced;

a cover-shaped flow channel formation member that is attached so as to cover the opening; and a cylindrical aerosol discharge port provided so as to pass through a portion of a top surface of the flow channel formation member located toward an outer edge thereof; wherein the case body and/or the flow channel formation member is provided with a rotation mechanism that, when the case body has overturned on a predetermined placement surface and the aerosol discharge port has become positioned on a lower side in a vertical direction of the top surface of the flow channel formation member, causes the case body to rotate in a circumferential direction of an outer circumferential surface of the case body so that a position of the aerosol discharge port moves away from the lower side in the vertical direction.

2. The nebulizer kit according to claim 1, wherein an extension member that extends outward in a diametric direction of the case body is provided in an outer surface of the case body and/or an outer surface of the flow channel formation member;

a leading end of the extension member is positioned further outward in the diametric direction of the case body than a tangent defined on an outer circumferential surface of the case body in a location closest to an inner circumferential surface of the aerosol discharge port, when viewed from above; and the rotation mechanism is configured so as to include the extension member.

3. The nebulizer kit according to claim 1, wherein a weight portion is provided in the case body and/or the flow channel formation member;

a straight line is defined by connecting an area of an outer circumferential surface of the case body that is closest to an inner circumferential surface of the aerosol discharge port and an area located directly opposite to the area in the outer circumferential surface of the case body, when viewed from above;

the weight portion is disposed so that a center of gravity of the weight portion and the straight line do not overlap, when viewed from above; and the rotation mechanism is configured so as to include the weight portion.

4. The nebulizer kit according to claim 1, wherein a grip that extends outward in a diametric direction of the case body is provided in an outer surface of the case body;

the grip is disposed in a position that, when the flow channel formation member is attached to the case body, is shifted in the circumferential direction from a side on which the aerosol discharge port is provided, when viewed from above; and the rotation mechanism is configured so as to include the grip.

5. A nebulizer comprising:

a nebulizer kit comprising:

a closed-ended, cylindrical case body that has an opening in an upper end, within which an aerosol is produced;

a cover-shaped flow channel formation member that is attached so as to cover the opening; and a cylindrical aerosol discharge port provided so as to pass through a portion of a top surface of the flow channel formation member located toward an outer edge thereof;

a main body including a compressor that discharges compressed air; and a compressed air tube portion including one end connected to the compressor and another end connected to the case body; wherein the case body and/or the flow channel formation member is provided with a rotation mechanism that, when the case body has overturned on a predetermined placement surface and the aerosol discharge port has become positioned on a lower side in a vertical direction of the to surface of the flow channel formation member, causes the case body to rotate in a circumferential direction of an outer circumferential surface of the case body so that a position of the aerosol discharge port moves away from the lower side in the vertical direction.

6. The nebulizer kit according to claim 1, wherein the cylindrical aerosol discharge port is configured to be connected to a mouthpiece, and when the cylindrical aerosol discharge port is not connected to the mouthpiece and the case body has overturned on the predetermined placement surface, the rotation mechanism causes the case body to rotate in the circumferential direction so that the position of the aerosol discharge port moves away from the lower side in the vertical direction.

7. The nebulizer kit according to claim 5, wherein the cylindrical aerosol discharge port is configured to be connected to a mouthpiece, and when the cylindrical aerosol discharge port is not connected to the mouthpiece and the case body has overturned on the predetermined placement surface, the rotation mechanism causes the case body to rotate in the circumferential direction so that the position of the aerosol discharge port moves away from the lower side in the vertical direction.

* * * * *